United States Patent [19]

Dahms

[11] 4,354,853

[45] Oct. 19, 1982

[54] KARL FISCHER REAGENT AND ITS USE

[76] Inventor: Harald Dahms, 472 Madison Ave., Toms River, N.J. 08753

[21] Appl. No.: 262,173

[22] Filed: May 11, 1981

[51] Int. Cl.$^3$ .................. G01N 31/16; G01N 33/18
[52] U.S. Cl. ........................... 23/230 R; 204/1 T; 252/408
[58] Field of Search .................. 23/230 R; 252/408; 204/1 T

[56] References Cited

U.S. PATENT DOCUMENTS 3,682,783  8/1972  Dahms et al. ................ 252/408 X
4,295,990  10/1981 Verbeek et al. ............... 23/230 R X

OTHER PUBLICATIONS

Chemical Abstracts, vol. 91, 1979, Abstract No. 91:13040s.
Verhoef et al., Electrochimica Acta, vol. 23, pp. 433–438, (1978).
Verhoef et al., J. Electroanal. Chem., vol. 71, pp. 305–315, (1976).
Verhoef et al., Analytica Chimica Acta, vol. 94, pp. 395–403, (1977).
Peters et al., Analytical Chemistry, vol. 27, pp. 450–453, (1955).
Karl Fischer, Angewandte Chemie, 48, 394 (1935).

*Primary Examiner*—Arnold Turk

[57] ABSTRACT

An improved method and reagent for determining the water content of a sample using a Karl Fischer type of reaction. The sample to be tested is placed in a vessel with a Karl Fischer type reagent. A known amount of a new titrant is then added to determine the water content of the sample, the new titrant including, preferably, only a halogen (such as iodine) and a solvent having high solubility for the halogen but very low solubility for water. An example of such a titrant solvent is xylene. The titrant is not affected by the presence of moisture in the atmosphere and does not lose its strength over prolonged periods of time. Because the reactions between the various constituents of the vessel solution-sample mixture and the titrant occur rapidly, the endpoint of the Karl Fischer reaction is much sharper than with the use of prior art reagents.

17 Claims, No Drawings

KARL FISCHER REAGENT AND ITS USE

DESCRIPTION

Technical Field

This invention relates to Karl Fischer type reagents for the determination of water in samples, and more particularly to an improved reagent for determining water content by the Karl Fischer reaction.

Background Art

The determination of moisture in materials such as liquids and solids by the Karl Fischer reaction is well known and widely used since it was first described by Karl Fischer in Angewandte Chemie 48, Pages 394-396 (1935). Numerous publications have also described this technique for water determination, and reference is made to a general text by J. Mitchell, Jr. and D. M. Smith, entitled, "Aquametry", published by Interscience in 1948.

In the Karl Fischer reaction, a sample containing water is introduced into a vessel solution where it is readily absorbed. The vessel solution may be an anhydrous reagent containing sulfur dioxide, a buffer, and an anhydrous solvent, usually methanol, formamide, methyl cellosolve (a trademark of Union Carbide), or mixtures thereof. A "titrant" containing iodine is introduced into the vessel solution and the sample to be analyzed and produces a reaction of the type $$H_2O + SO_2 + I_2 = 2HI + SO_3$$

In this Karl Fischer reaction, the water to be determined reacts with iodine on a quantitative basis; consequently, the amount of reacted iodine is a measure of the amount of water present in the sample. The titrant is generally a methanolic solution of iodine and is introduced into the vessel containing the sample and the vessel solution until no more iodine is used up; that is, an end point of the reaction is reached. Since the iodine was introduced via the titrant, the amount of titrant used is a measure of the amount of water in the sample to be tested.

Several Karl Fischer reagents are commercially available and in use. For example, the Karl Fischer reagent offered by Harleco Company of Gibbstown, New Jersey contains, per liter, 325 ml pyridine as a buffer, 142 grams iodine, and 65 grams sulfur dioxide, all of which are dissolved in methyl cellosolve (2-methoxyethanol).

Another reagent presently being used is that offered by the Baker Chemical Company of Phillipsburg, New Jersey, which is a methanolic solution of iodine as a titrant, and a methanolic solution of sulfur dioxide and a buffer (sodium acetate) as a solvent. Other common solvents are formamide or alcohol ethers.

Still another reagent and method for the Karl Fischer determination of water is that described in U.S. Pat. No. 3,682,783. The reagent of that patent uses an increased amount of sulfur dioxide in order to prevent excessive cycling at the end of a titration, thereby providing a more correct reading of the endpoint of the reaction.

The following references discuss various aspects of Karl Fischer titrations and provide a more detailed analysis of the Karl Fischer reaction.

1. J. C. Verhoef and E. Barendrecht, Electrochimica Acta, Vol. 23, pp. 433-438 (1978)
2. J. C. Verhoef and E. Barendrecht, J. Electroanal. Chem. 71, pp. 305-315 (1976)
3. J. C. Verhoef and E. Barendrecht, Analytica Chimica Acta, 94, pp. 395-403 (1977)
4. E. D. Peters, J. L. Jungnickel, Anal. Chemistry, Vol. 27, p. 450 (1955)

When $SO_2$ is dissolved in methanol it takes part in the equilibrium $$SO_2 + CH_3OH = CH_3-O-SO_2^- + H^+.$$

(methylsufite ion)

It is this methylsulfite ion which reacts fast with iodine in the Karl Fischer reaction (not the $SO_2$) to increase the concentration of methylsulfite ion and to bind the gaseous $SO_2$. The solvent also has to contain a buffer which binds the $H^+$ in the reaction. As mentioned previously pyridine has often been used as a buffer, wherein $$pyridine + H^+ = pyridine - H^+.$$

A more recently used buffer is acetate, such as sodium acetate, wherein $$acetate^- + H^+ = H.acetate$$

(acetic acid)

Any other salt which binds $H^+$ ions can be used, where the system of salt and its acid is called the "buffer". Hence, all Karl Fischer reagents can be described in general as consisting of sulfur dioxide and a buffering system (pyridine, sodium acetate, etc.).

The Peters et al reference considers the advantages of 2 methoxy-ethanol over methanol, while reference 3 shows the application of other buffers besides pyridine. Reference 3 shows that some reactants in this equation ($SO_2$, HI, and $SO_3$) may be involved in reaction equilibria with the solvent and the buffer before and after the Karl Fischer reaction given above. For example, $SO_2$ may have to react with the buffer and the solvent before reacting with iodine and water. However, as will be described in more detail later, the present invention is not concerned with specific reaction mechanisms but with the general Karl Fischer reaction involving the reaction of water with iodine, sulfur dioxide, and a buffer in a solvent or mixture of solvents.

In his early experiments, described in Angewandte Chemie 48, 394 (1935), Karl Fischer used benzene as a solvent for the combined reagent, containing $I_2$ as well as pyridine and $SO_2$. He found that pyridine salts were precipitated and, therefore, he abandoned benzene in favor of methanol. It should be noted that the use of benzene is different from the present invention in that the present invention uses only $I_2$ in the benzene titrant (when benzene is the titrant solvent) while pyridine and $SO_2$ are in the vessel solution (which is, for example, a methanol solution). Indeed, the presence of pyridine in the titrant of the present invention would run counter to the present invention since pyridine attracts and absorbs atmospheric moisture and would render the titrant of the present invention unstable.

All presently used Karl Fischer reagents have certain disadvantages, one of the most important being that the reagent rapidly attracts water from the atmosphere and this water absorption changes the "titer" (i.e., strength) of the titrant. Therefore, frequent standardization of the titrant is required. Additionally, this same problem means that elaborate measures must be undertaken to protect the reagent from water absorption. In the titration apparatus used to determine water content, various drying tubes are required to ensure that water vapor from a source other than the sample does not enter the reagent.

Another disadvantage with present Karl Fischer reagents relates to their slow decomposition over a period of time. This means that the shelf life of such reagents is poor, and that the titer of the solution does not remain constant.

The titrants of the present invention have other advantages in addition to those (constant strength and moisture insensitivity) described above. These other advantages relate to the rapid acquisition of a "true" endpoint for the titrations. In order to more fully understand this advantage, a titration using the presently available reagents will be described in more detail. Thus, present titrations proceed to the endpoint of the titration when very little water is left in the vessel. In this situation, the rate at which iodine is consumed is slow. Due to this slow reaction, an excess of iodine may appear even though small amounts of water are still present in the sample. This is called a "false" endpoint. After some time, usually a few seconds, the iodine has reacted with water and some more iodine titrant has to be added. Some more false endpoints may appear until the "true" endpoint is reached. The true endpoint (i.e., the endpoint indicating that all water in the sample has reacted with the iodine) will hold for a long time. Most present procedures call for a time of 20 or 30 seconds for the endpoint to hold, in order to term it a true endpoint.

This slow reaction time leading to false endpoints is not only an inconvenience, but also is a factor which may lead to some error. A prolonged titration gives the iodine a chance to be consumed via side reactions, i.e., reactions with species other than water. The problem of false endpoints has been recognized in the art and is, for example, addressed for coulometric titrations in the aforementioned U.S. Pat. No. 3,682,783.

As will be more fully apparent, the occurrence of false endpoints is related to the rate of the reaction. That is, the number of false endpoints increases as the rate of the reaction decreases. Thus, one of the objects of the present invention is to provide improved titrants having faster reaction rates and therefore fewer false endpoints.

Since the Karl Fischer reaction is extensively used to determine water concentration in test samples, a solution to these problems would be extremely advantageous. Accordingly, it is a primary object of the present invention to provide a stable Karl Fischer type reagent whose strength does not change over the passage of time.

It is another object of the present invention to provide an improved Karl Fischer type reaction for the determination of water in samples in which the adverse effects of water contamination by other than the sample are minimized.

It is another object of the present invention to provide an improved Karl Fischer type of titration method which does not require a complex apparatus involving many drying tubes, etc.

It is another object of the present invention to provide a Karl Fischer type of titration process in which the Karl Fischer type reagent need not be standardized before a sample is measured.

It is another object of the present invention to provide an improved Karl Fischer type reagent in which a sharper end point is obtained from the reaction to determine water content.

It is another object of the present invention to provide an improved Karl Fischer type of titration process for the determination of water, in which the reagent composition is employed in two parts: the titrant and the vessel solution in which the sample is placed, where the solvents of the two parts are not the same.

Disclosure of Invention

In this invention, the Karl Fischer type reaction process is carried out as it normally is in the art. However, the reagent composition comprises two parts: one part is the vessel solution into which the sample to be measured is introduced, while the other part is the "titrant" which is added to the combination of the sample and the vessel solution in a measured amount in order to determine the amount of water in the sample. The vessel solution readily dissolves water while the titrant does not dissolve water in any appreciable amount.

The vessel solution into which the sample is introduced can, for example, contain pyridine or another buffer and sulfur dioxide, and can be the conventionally used Karl Fischer reagents, such as methanolic solutions of sulfur dioxide and sodium acetate. Preferred solvents include methanol, methyl cellosolve, formamide and other solvents which are used in conventional Karl Fischer reagents.

This invention is not directly dependent on the details of the reaction mechanism. As long as the vessel solution reacts with the titrant of the present invention and water in a stoichiometric fashion, as follows, $I_2$(titrant)+$H_2O$(sample)+$SO_2$(bound in any form)=$2HI$+$SO_3$(bound or reacted in any form), the present titrants will offer many advantages. These titrants will work with the old pyridine-$SO_2$ solution as well as with newer systems of the type described in the aforementioned J. C. Verhoef et al references.

The titrant has an extremely low solubility for water, but a good solubility for iodine. A preferred solvent in the titrant contains xylene, although other titrant solvents than xylene will be described.

Since the titrant does not readily dissolve water, its strength does not change and standardization is not required for each sample measurement. Additionally, the titration apparatus can be simplified, since drying tubes are not needed in the portion of the apparatus containing the titrant. The titrant has an excellent shelf life and, surprisingly, a sharper endpoint is provided through its use than has been obtained with prior art reagents.

These and other objects, features, and advantages will be more readily apparent from the following more particular description of the preferred embodiments.

Best Mode for Carrying Out the Invention

The actual water determination in this invention is performed in a manner similar to the performance of any Karl Fischer titration. However, because the titrant is different than that previously used, many advantages result as will be described in more detail.

In the method, a certain volume, for example 50 ml, of the vessel solution containing $SO_2$ and a buffer is stirred in a vessel which is protected from atmospheric moisture. This protection of the vessel solution is obtained by the use of drying tubes, etc., as is well known in the art. A non-water absorbing titrant containing iodine and a titrant solvent for iodine (such as xylene) is then added from a buret until all water traces in the vessel solution are reacted, as indicated by an electrometric measuring device as known in the art. A known amount of sample, the water content of which has to be determined, is added to the vessel solution. A measured volume of the iodine containing titrant is then added to the vessel solution-sample mixture until the endpoint of the titration is again reached. The measured volume of titrant consumed is a measure of the water contained in the test sample.

The advantages of this invention are readily apparent to those of skill in the art. Using a titrant which does not attract moisture and is indefinitely stable means that it will maintain its known strength (that is, a certain volume of the titrant is always equivalent to the same amount of water). In contrast to this, prior art solutions decrease in strength with handling and time, thereby necessitating frequent calibration. Also, no protection from the atmosphere is required for the titrant of this invention. Another important advantage, which is totally unexpected, is that the iodine and buffer-sulfur dioxide appear to react faster and thereby produce a sharper endpoint than is obtained by the use of conventional Karl Fischer reagents.

In the practice of this invention, the titrant solvent is different than the vessel solution in which the test sample is introduced. The most suitable titrant solvents contain a benzene ring such as dimethylbenzene (=xylene) and methylbenzene (=toluene) or, more generally, compounds of the type benzene-R, where R is one or more side groups (such as aliphatic groups or halogens) connected to the benzene ring.

The following titrant solvents have been used for preparing the iodine containing titrant, either singly or in combination: benzene, toluene, xylene, chloroform, trichloroethylene, 111-trichlorethane, carbon tetrachloride, 1,1 dichloroethane, 1,2 dichloroethane, 1,1,2 trichloroethane, dichloromethane, and other halogenated hydrocarbons of the general formula $C_nH_{2n+2-m}X_m$, where X is a halogen or a combination of them, n is in the range from 1 to 8, and m is in the range from 1 to $2n+2$.

A variety of benzene derivatives is also suitable. Such derivatives include halogenated benzene, for example, chlorobenzene, dichlorobenzene, chlorotoluene, dichlorotoluene, monochloroxylene, dichloroxylene, where the chlorogroup can be either attached to the benzene ring or to the methyl-group. They also include benzene derivatives with aliphatic side chains such as toluene, xylene, propylbenzene, etc. Other suitable solvents in the titrant are halogenated compounds, such as, for example, chlorinated toluenes or xylenes.

It is also understood that the titrant may contain small amounts of other solvents as long as they do not substantially increase the ability to absorb water and decrease the solubility for iodine.

A number of titrants has been tested for false endpoints (i.e., slow reaction rates). As was pointed out earlier, the number of false endpoints increases as the reaction rate decreases. These tests were carried out in the following manner, which was identical for all titrants. 50 ml of vessel solution (a methanol solution containing 280 g pyridine as a buffer and 80 g sulfur dioxide per liter) was used. After pre-titration to remove water traces from the vessel solution, 10 milligrams of water were added. The titrant was then added to the vessel solution from a buret at a slow, constant rate of 0.1 ml per second. The titrant contained 56.4 g of iodine per liter. The addition of titrant to the vessel solution was continued until a first "endpoint" was reached. The titrant consumed up to that first (false) endpoint was noted.

The titration was then continued until the true endpoint was reached. This was the endpoint which held for 20 seconds. An earlier false endpoint can be considered an indication of a slow reaction rate (which is undesirable). The following table shows the results for a number of iodine titrant solutions. This table compares reaction rates as measured by the appearance of first (false) endpoints for various titrants and vessel solutions. As is apparent, if the volume of titrant consumed until the first false endpoint is reached is large, the reaction rates proceed quickly and less false endpoints will be achieved.

In this table, the true endpoint for all solutions was 2.5 ml of titrant. This table also shows the results of the same experiment conducted for two or more solvents, 2-methoxyethanol and formamide, each containing 280 g pyridine as a buffer and 80 g sulfur dioxide per liter.

The table indicates that xylene-iodine is the best solution, followed by toluene-iodine and benzene-iodine. It is further evident that the benzene ring containing compounds (xylene, toluene, benzene) as a group are better than the previously used methanol, 2-methoxyethanol, or formamide. Another desirable group consists of aliphatic halogenated compounds chloroform, 111-trichloroethane, and trichloroethylene.

TABLE

Comparison of reaction rates as measured by appearance of first false endpoint for various titrants and vessel solutions.

| Titrant 56.4 g Iodine Dissolved in 1l | Volume of Titrant Consumed Until First False Endpoint is Reached (In milliliters of solvent) | | |
|---|---|---|---|
| | Methanol | 2-Methoxy-ethanol | Formamide |
| Methanol | 1.8 | 1.9 | 1.8 |
| 2-Methoxyethanol* | 1.65 | 1.7 | 1.7 |
| Benzene | 2.0 | 2.05 | 2.0 |
| Toluene | 2.2 | 2.1 | 2.25 |
| Xylene | 2.35 | 2.2 | 2.3 |
| 50% Xylene-50% Toluene | 2.3 | 2.1 | 2.2 |
| Ethanol | 1.75 | 1.6 | 1.6 |
| Formamide | 1.85 | 1.9 | 1.8 |
| Chloroform | 2.1 | 2.1 | 2.25 |
| 111-Trichloroethane | 2.0 | 2.05 | 2.1 |
| Trichloroethylene | 1.9 | 1.95 | 1.9 |

*Sold under the trade name "methylcellosolve" by Union Carbide Corporation. It is also known as ethylene glycol monomethyl ether.

EXAMPLE

In a typical example, the titrant solution consists of an iodine-xylene solution containing 56.4 grams of iodine per liter. Since iodine and water react on a 1:1 basis, every ml of this titrant will use up 4 mg of water. This is determined by multiplying the amount of iodine times the ratio of the molecular weight of water to the molecular weight of iodine.

As a vessel solution into which the test sample is introduced, 255 g of pyridine as a buffer and 95 g of sulfur dioxide are diluted into one liter of methanol (the methanol should contain as small an amount of water as possible). If these components contain small amounts of water, it is also suitable to add small amounts of iodine so that the water traces in the vessel solution are consumed. The amount of pyridine and $SO_2$ can vary widely as long as there is an excess of them compared to the amount of iodine.

Having this titrant solution and vessel solution, the actual water determination is performed as described previously.

In the practice of this invention, the new titrant solutions can be used with any type of Karl Fischer type reagent. For example, instead of using pyridine and $SO_2$ in methanol, a methanolic solution of sodium-acetate and sulfur dioxide may be used. Sodium acetate and sulfur dioxide will react in methanol to form acetic acid and sodium monomethylsulfite, as discussed in reference 3 of J. C. Verhoef et al. Generally, any system which reacts with iodine would benefit from use with these new titrants. Additionally, many modifications may be made to the titrant. The main requirement is simply that the titrant must have a low solubility for water; for example, xylene has a solubility for water of less than 200 mg/l. Further, the titrant should have a good solubility for iodine, that is, more than 1 g/l. The titrant should also have a moderate vapor pressure (i.e., experience little evaporation), and the titrant must be miscible with the vessel solution. Also, there must be little reaction between the iodine and the solvent used in the titrant.

While this invention has been described with respect to certain examples, it will be appreciated by those of skill in the art that the invention encompasses using a different titrant solvent than the solvent used in the vessel solution, where the titrant solvent has good solubility for iodine but very little solubility for water. While there can be traces of, for instance, a buffer and sulfur dioxide, in the titrant, it is preferable to have iodine alone in the titrant solution. This is because the solvents for these other materials are also solvents for water, and this is what is to be avoided in the titrant solution.

The vessel solution, on the other hand, is preferably a good solvent for water so that the water in the sample is readily dissolved in it. It is most preferable that the titrant has a solubility for water of less than 1 mg/ml while the vessel solution has a solubility for water of more than 1 mg/ml.

The term "Karl Fischer reaction (reagent)" has been used in a wider sense than in the early work of Karl Fischer. It includes many modifications which were developed by other people in succeeding years. For example, the use of other solvents mentioned in this specification, such as formamide, methanol-chloroform mixtures, etc., were developed subsequent to Karl Fischer's initial experiments. Another example relates to the use of mixtures of these solvents with chloroform, etc. in order to dissolve fatty compounds such as margarine.

In more general terms, the "Karl Fischer type solvent" contains sulfur dioxide and a buffer in a suitable solution. Examples of such buffers are pyridine and sodium acetate. As described by Verhoef et al in aforementioned reference 3, such buffers may have the function to bind sulfur dioxide and convert it into a species ($CH_3SO_3^-$) that readily participates in the Karl Fischer reaction. According to Verhoef et al, $SO_2$ reacts with methanol in the reaction $SO_2 + CH_3OH = CH_3SO_3^- + H^+$, or in general terms $SO_2 + ROH = RSO_3^- + H^+$.

A buffer is then simply any substance that binds the $H^+$ ion and thereby shifts the reaction equilibrium towards the right side of the equation. Already mentioned examples of such buffers are pyridine and sodium acetate. However, to those skilled in the art, it is apparent that many other compounds bind hydrogen ions and may, therefore, be suitable buffers: for example, sodium salicylate, sodium trichloroacetate and many other compounds too numerous to mention. It will be appreciated that they can be used in the present invention.

From the foregoing, it is also apparent that the term "sulfur dioxide" as used in the application includes species that sulfur dioxide may form when reacting with the solvent and the buffer. Thus, the invention broadly relates to Karl Fischer type reagents, rather than to only the specific reagents used by Karl Fischer in his initial experiments.

One of the main features of this invention is the stable titrant solution containing iodine. Therefore, any modifications of the Karl Fischer method which use a reaction with iodine will benefit from this improvement. For example, a recent reagent modification marketed by the J. T. Baker Company uses a titrant of an iodine-methanol solution and a vessel solution of sodium methylsulfite (created by the reaction of $SO_2$, sodium acetate and methanol) and acetic acid in methanol. This vessel solution has been used in combination with the present iodine-xylene solutions, as well as with others of the inventive iodine solutions. In all cases, excellent results were obtained.

Since the titrants of the present invention have a substantially constant strength, there is no need for extensive calibration prior to each titration. Thus, an operator can visually determine the titration endpoint and know that the amount of titrant consumed is exactly related to the amount of water in the sample.

In accordance with some of the other modifications described previously, experiments were undertaken in which pyridine was not used in the vessel solution. Instead, other bases such as aniline, known in the art, were used with good results.

Consequently, in more general terms, the improvement of the present invention pertains to all Karl Fischer type reactions which react with (1) a halogen containing solution or (2) a solution which reacts on a stoichiometric basis with water and a reducing agent ion ($SO_2$, methylsulfite), for the purpose of determining the amount of water in a sample. Of course, it will be apparent to those of skill in the art that a nonreacting substance can be put into the titrant for different purposes. For example, an oil can be added to prevent evaporation, as long as the solubility of the titrant for water remains less than 1 mg/ml.

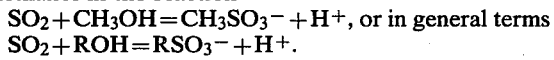

Simplified Titration Apparatus

Digital titrators are known in the art, reference being made to the digital titrators marketed by the Hach Chemical Company, Loveland, Colorado and Brinkmann Instruments, Inc., Westbury, New York. These digital titrators provide a direct digital readout of the volume discharged from the titrator during a titration. The use of the titrants of this invention provide special advantages when used in a digital titrator. For example, since the present titrants have a constant, stable titer, the titrant can be prepared such that the digital readout (without any computation) is directly in "micrograms of water". For example, if the titer of the titrant is 10 milligrams of water per milliliter, a digital readout of 4.57 milliliters means 45.7 milligrams of water were present in the sample.

A further advantage is that a simple, hand-held digital titrator of the type marketed by Hach Chemical Company can be used. Since the stable titrants of this invention are not sensitive to the open atmosphere, the digital titrator can be filled simply by sticking it into the supply bottle containing the titrant. When the titrator is filled, digital titration of the sample can immediately begin.

Pre-titration of the moisture in the vessel solution is particularly convenient using the present titrants and a digital titrator. The vessel solution is pretitrated with the titrator to the endpoint. Then the digits are simply reset to zero, followed by the actual titration which can be immediately started.

A very inexpensive and simple titration instrument can be provided for use with the present titrants. In this instrument, a simple glass tube attached to a syringe, and an attached paper scale, are suitable. The paper scale is in units of micrograms of water and is slidable along the glass tube. A capped vessel contains the vessel solution and the sample, the syringe being directly insertable through the cap (such as a rubber cap) located over the vessel. After pre-titration, the paper scale can be slid up and down the glas tube so that the zero mark on the scale coincides with the level of the titrant in the glass tube. The titration is then carried out by slowly depressing the syringe plunger until the endpoint is reached. This is determined optically by viewing the color change of the solution in the vessel when the titrant is added. The water content of the sample is then directly read from the paper scale. This simplified and inexpensive apparatus can be carried by an operator into the field for quick and accurate sample measurements. Because very sharp endpoints result when the titrants of the present invention are used, this inexpensive visual titration kit is particularly suited for widespread use under a variety of field conditions.

In the most preferred practice of this invention, a titrant is used containing a halogen and a solvent having a benzene ring. These solvents provide high reaction rates and sharp endpoints, in addition to increased accuracy in successive titrations. The substance providing the benzene ring in the solvent is present in an amount greater than 50% of the solvent, by weight. Preferably, xylene, toluene, and benzene are used as the benzene ring-containing materials, although it is possible to add other materials to the titrant, as long as the titrant does not lose its good solubility for the halogen and its very low solubility for water. Of course, mixtures of xylene, toluene, and benzene can also be used.

While the invention has been particularly shown and described with reference to preferred embodiments thereof, it will be understood by those skilled in the art that the foregoing and other changes in form and details may be made therein without departing from the spirit and scope of the invention.

Having thus described my invention, what I claim as new, and desire to secure by Letters Patent is:

1. A method for determining water by a Karl Fischer type reaction, including the titration of a vessel solution containing a water sample with a halogen-containing titrant, including the steps of:
    combining said water containing sample and a vessel solution including a reducing substance and a first solvent for said reducing substance, said solvent having a high solubility for water,
    adding a titrant to said vessel solution-water sample combination, said titrant including a halogen and a second solvent for said halogen wherein said second solvent is different than said first solvent, has a very low solubility for water, and includes as said second solvent at least a substance selected from the group consisting of xylene, toluene, and mixtures thereof, said titrant reacting with said vessel solution-water sample combination on a stoichiometric basis, the amount of titrant used being related to the amount of water in said sample.

2. The method of claim 1, where said halogen is selected from the group consisting of iodine and bromine.

3. In a method for determining water by a Karl Fischer type reaction including the titration of a water containing sample with a halogen-containing titrant, the improvement comprising said method wherein
    said halogen-containing titrant consists of a solution of a halogen selected from the group consisting of iodine and bromine in a first solvent including as said first solvent at least a substance selected from the group consisting of xylene, toluene, benzene, chloroform, carbon tetrachloride and mixtures thereof, and
    wherein said water-containing sample is dissolved in a vessel solution containing reactants necessary to produce a Karl Fischer type reaction when titrated by said titrant, said reactants being dissolved in a second, different solvent having a high solubility for water.

4. The method of claim 3, where said second solvent is selected from the group consisting of methanol, 2 methoxyethanol, formamide, and mixtures thereof.

5. The method of claim 3, where said reactants include a reducing substance selected from the group consisting of sulfur dioxide and species that $SO_2$ forms when reacting with said reactants in said vessel solution.

6. The method of claim 3, where said reactants include a reducing substance and a buffering substance.

7. The method of claim 6, where said buffering substance is selected from the group consisting of pyridine, aniline, acetates, and salts which bind $H^+$ ions.

8. In a method for determining the water content of a sample by a Karl Fischer type reaction including the titration of a water containing sample with a halogen-containing titrant, the improvement wherein
    said water containing sample is dissolved in a vessel solution including a reducing substance selected from the group consisting of sulfur dioxide and species that sulfur dioxide forms when reacting with said vessel solution, and a first solvent for said sample and said reducing substance, said solvent having a high solubility for water and being selected from the group consisting of methanol, 2-methoxyethanol, formamide and mixtures thereof and
    wherein said titrant includes a halogen dissolved in a second solvent having a very low solubility for water and a high solubility for said halogen, said second solvent including as said second solvent at least a substance selected from the group consisting of xylene, toluene, and mixtures thereof, said titrant reacting with said vessel solution and water on a stoichiometric basis wherein the amount of titrant consumed is related to the amount of water in said sample.

9. The method of claim 8, where said halogen is iodine.

10. The method of claim 8, where said vessel solution includes a buffering substance selected from the group consisting of pyridine, aniline, acetic acid, and salts which bind H+ ions.

11. In a method for determining the water content of a sample by a Karl Fischer type reaction including the titration of a solution consisting of a reducing substance, a buffer which binds H+ ions, said water containing sample, and a first solvent, with a titrant, the improvement wherein said titrant contains iodine and a second solvent different from said first solvent and having a very low solubility for water, said second solvent being present in said titrant in an amount at least 50% by weight and being selected from the group consisting of xylene, toluene, benzene, chloroform, carbon tetrachloride, and mixtures thereof.

12. In a method for determining the water content of a sample by a Karl Fischer type reaction including the titration of a vessel solution with a titrant, the improvement comprising a vessel solution containing in a first solvent said sample, a reducing agent, and a buffer to bind H+ ions in said vessel solution having a high solubility for water in excess of 1 mg/ml, and a titrant containing iodine and a second solvent different than said first solvent and having a low solubility for water less than 1 mg/ml, said second solvent including as said second solvent a substance selected from the group consisting of xylene, toluene, benzene, chloroform, carbon tetrachloride, and mixtures thereof.

13. In a method for determining the water content of a sample by a Karl Fischer type reaction including the titration of a vessel solution with a titrant, the improvement comprising a vessel solution prepared by combining $SO_2$, a buffer, said sample, and a first solvent, said vessel solution having a high solubility for water, and a titrant including iodine and a second solvent different than said first solvent, said titrant having a low solubility for water less than 1 mg/ml, wherein said titrant reacts stoichiometrically with said water containing vessel solution to an endpoint wherein the amount of titrant consumed is related to the amount of water in said sample.

14. In a method for determining the water content of a sample by a Karl Fischer type reaction, the steps of:

forming a solution including said sample, a reducing agent, a buffer to bind H+ ions, and a first solvent, said solution having a high solubility for water, and digitally titrating said solution with a titrant including iodine and a second solvent different than said first solvent and having a low solubility for water, said second solvent containing at least 50% by weight of a substance selected from the group consisting of xylene, toluene, benzene, and mixtures thereof.

15. In a method for determining the water content of a sample by a Karl Fischer type of reaction, the steps of:

forming a solution including said sample, a reducing agent, a buffer, and a first solvent, said solution having a high solubility for water greater than 1 mg/ml, and titrating said solution with a titrant including iodine and a second solvent, said second solvent containing a substance having a benzene ring, said substance being present in said solvent in an amount greater than 50%, by weight.

16. In a method for determining the water content of a sample by a Karl Fischer type reaction including the titration of a vessel solution with a titrant, the improvement comprising a vessel solution containing in a first solvent said sample, $SO_2$, and a buffer to bind H+ ions in said vessel solution having a high solubility for water in excess of 1 mg/ml, and a titrant containing iodine and a second solvent having a low solubility for water less than 1 mg/ml, said second solvent containing as said second solvent a substance selected from the group consisting of xylene, toluene, and mixtures thereof in an amount at least 50% by weight.

17. The method of claim 16, where said vessel solution contains methanol.

* * * * *